(12) United States Patent
Zhang et al.

(10) Patent No.: US 11,180,437 B2
(45) Date of Patent: Nov. 23, 2021

(54) METHOD FOR PREPARING 1,3-DICARBONYL COMPOUND BASED ON METAL HYDRIDE/PALLADIUM COMPOUND SYSTEM

(71) Applicant: SOOCHOW UNIVERSITY, Suzhou (CN)

(72) Inventors: Shilei Zhang, Suzhou (CN); Yujian Mao, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 17/203,097

(22) Filed: Mar. 16, 2021

(65) Prior Publication Data
US 2021/0206708 A1  Jul. 8, 2021

Related U.S. Application Data

(63) Continuation of application No. PCT/CN2018/106060, filed on Sep. 17, 2018.

(51) Int. Cl.
| | | |
|---|---|---|
| *C07C 45/41* | (2006.01) | |
| *B01J 23/00* | (2006.01) | |
| *B01J 31/00* | (2006.01) | |
| *B01J 23/44* | (2006.01) | |
| *B01J 31/12* | (2006.01) | |
| *C07C 49/553* | (2006.01) | |

(52) U.S. Cl.
CPC ............. *C07C 45/41* (2013.01); *B01J 23/44* (2013.01); *B01J 31/121* (2013.01); *C07C 49/553* (2013.01)

(58) Field of Classification Search
CPC .......... C07C 45/41; B01J 23/44; B01J 31/121
See application file for complete search history.

(56) References Cited

U.S. PATENT DOCUMENTS

2006/0020012 A1  1/2006  Jones et al.

FOREIGN PATENT DOCUMENTS

| CN | 102491886 A | 6/2012 |
|---|---|---|
| CN | 102863376 A | 1/2013 |
| CN | 108976122 A | 12/2018 |
| CN | 109053446 A | 12/2018 |

OTHER PUBLICATIONS

Gang Ding et al., "Progress in Palladium-Catalyzed Tandem Reaction of Constructing Benzo-Five-Membered Heterocycles" Chinese Journal of Organic Chemistry, 2016, 36, 43-59 (Dec. 31, 2016).

*Primary Examiner* — Sikarl A Witherspoon
(74) *Attorney, Agent, or Firm* — SZDC Law P.C.

(57) ABSTRACT

Disclosed is a method for preparing a 1,3-dicarbonyl compound based on a metal hydride/palladium compound system. The method includes the following steps: suspending a palladium compound and a metal hydride in a solvent under the protection of nitrogen, then adding an electron-deficient olefin compound, reacting same at 0° C.-100° C. for 0.3 to 10 hours, then adding a saturated ammonium chloride aqueous solution to stop the reaction, and then subjecting same to extraction, evaporation until dryness, and column chromatography purification to obtain the 1,3-dicarbonyl compound. The hydride and palladium compound catalysts used by the present invention are reagents easily obtained in a laboratory. Compared to a common hydrogen hydrogenation method, the method is easier to operate, and has a higher safety, mild conditions, and a high reaction yield.

10 Claims, No Drawings

METHOD FOR PREPARING 1,3-DICARBONYL COMPOUND BASED ON METAL HYDRIDE/PALLADIUM COMPOUND SYSTEM

This application is a Continuation Application of PCT/CN2018/106060, filed on Sep. 17, 2018, which is incorporated by reference for all purposes as if fully set forth herein.

TECHNICAL FIELD

The present invention relates to the technical field of organic synthesis, and particularly relates to the application of a metal hydride/palladium compound system in preparing 1,3-dicarbonyl compounds with a Michael-Dieckmann cascade reaction of an electron-deficient olefinic compound, and more particularly relates to a method of preparing a 1,3-dicarbonyl compound based on metal hydride/palladium compound system.

BACKGROUND TECHNIQUE

Sodium hydride is a strong base often used in the laboratory and industry. For a long time, there have been few reports about its use as a reducing agent. Existing technologies using sodium hydride require a large excess of sodium hydride (more than 5 equivalents), and at least 2 equivalents of sodium iodide are required as accelerators.

Reduction of electron-deficient olefinic compounds is a common chemical conversion to produce corresponding saturated carbonyl compounds. This type of reaction generally uses hydrogen/palladium-carbon conditions for reduction; in addition, some hydrogen negative reagents would reduce the electron-deficient double bond, such as $[(Ph_3P)CuH]_6$ (Stryker reagent), $R_3SiH$, Hantzsch esters, etc. However, these reactions are dangerous more or less, such as explosive hydrogen, expensive reagents, the lack of atomic economy, and more waste to be processed after the reaction, such as $[(Ph_3P)CuH]_6$ (Stryker reagent), $R_3SiH$, Hantzsch ester, etc.

SUMMARY OF THE INVENTION

Technical Problems

The technical problem to be solved by the present invention is to provide the application of a metal hydride/palladium compound system, which is in preparation of 1,3-dicarbonyl compound 3 with a Michael-Dieckmann cascade reaction of electron-deficient olefinic compound 1 with ortho ester group substituent.

Technical Solutions

The present invention adopts the following technical solutions:

A method of preparing 1,3-dicarbonyl compound based on metal hydride/palladium compound system comprising: under the protection of nitrogen, stirring suspended palladium compound and metal hydride are in a solvent, then add the electron-deficient olefin compound, the reaction is performed at 0° C. to 100° C. for 0.3 to 10 hours, to obtain the 1,3-dicarbonyl compound.

In the Michael-Dieckmann reaction of the present invention, the metal hydride is used as a reducing agent, palladium and its salts are used as a catalyst, and the electron-deficient olefin compound is a substrate to react in solvent to obtain the cascade reaction product 1,3-dicarbonyl compound.

In the present invention, the metal hydride is sodium hydride, lithium hydride, potassium hydride or calcium hydride; preferably, sodium hydride or lithium hydride; more preferably, sodium hydride.

In the present invention, the palladium compound is palladium chloride, palladium acetate, $Pd_2(dba)_3$, $Pd(TFA)_2$, $[(\eta^3-C_3H_5)PdCl]_2$, $Pd(dppp)Cl_2$, $Pd(C_6H_5CN)_2Cl_2$, $Pd(OH)_2$; preferably, palladium chloride and palladium acetate; and more preferably, palladium chloride.

Beneficial Effects of the Present Invention

Beneficial Effects

The Michael-Dieckmann cascade reaction with sodium hydride/palladium has the following advantages: 1) Comparing with the other reducing agents, sodium hydride is cheaper; compared with hydrogen reduction, the sodium hydride method is safer. 2) Sodium hydride has a small molecular weight and simple composition, and the amount used in the reaction is small, so using sodium hydride as a reducing agent is an atomic economic method; by-products include harmless sodium salt, and no other waste is generated. 3) Sodium hydride and palladium catalysts are reagents commonly used in the laboratory, which is very convenient to use. 4) Compared with Stryker reagent, the combined price of sodium hydride/palladium is much cheaper, and the palladium reagent can be recycled, so it is more suitable for laboratory and industrial applications.

The electron-deficient olefin compound has the following structure:

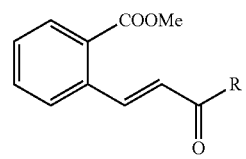

R is aryl, alkyl, alkoxy, amino group etc.

In the present invention, a molar ratio of the palladium compound:the metal hydride:the electron-deficient olefin compound is (0.01 to 1):(1 to 5):1; preferably, the molar ratio of the palladium compound:the metal hydride:the electron-deficient olefin compound is (0.05 to 0.15):(1 to 3):1; more preferably, the molar ratio of the palladium compound: the metal hydridea:the electron-deficient olefin compound is 0.1:(1.5 to 2.5):1; and most preferably, the molar ratio of the palladium compound:the metal hydride:the electron-deficient olefin compound is 0.1:2:1.

The technical solution above can be expressed as follows:

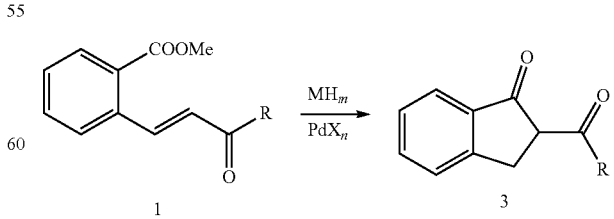

Wherein R is aryl group, alkyl group, alkoxy group, amino group, etc.; M is a metal, such as lithium, sodium, potassium, or calcium, etc.

The conversion from compound 1 to compound 3 in the convention art can be completed in steps, for example, first reducing the double bond with hydrogen, and then treating with alkali to obtain 3; it can also be completed in one pot reaction using Stryker reagent, i.e., conducting a Michael type conjugate reduction reaction of the double bond in compound 1 and a Dieckmann reaction to obtain compound 3. In this process, the stepwise reaction operation is complicated, the cost is high, and the waste generated is large. Although the one-pot reaction is simple, the Stryker reagent is very expensive (1 g>500 Chinese yuan). Therefore, the overall cost is actually higher than the step-by-step method.

In the above technical solution, after the reduction reaction, add saturated ammonium chloride aqueous solution to stop the reaction, and then the product is subjected to extraction, drying, rotary evaporation, and column chromatography to obtain the 1,3-dicarbonyl compound.

In the above technical solution, the solvent is DMA, DMF, THF, DME or dioxane.

In the above technical solution, the reaction temperature of the reaction is 25 to 60° C.; and the reaction time of the reaction is for 0.3 to 2 h.

Generally, to prepare 1,3-dicarbonyl compound 3 from an ortho-ester-substituted electron-deficient olefinic compound 1 includes two methods: the first one is the hydrogen/palladium-carbon hydrogenation reduction of double bond, and then Dieckmann condensation occurs under basicity. In this process, the use of hydrogen is a potentially dangerous factor, which can cause fire and explosion if improperly handled. The second is the direct series reaction with the more expensive Stryker reagent. Therefore, it is of great significance to use a metal hydride in the Michael-Dieckmann cascade reaction, which is relatively safe and inexpensive; more importantly, this method uses the reducibility and alkalinity of sodium hydride, and is very atomic economic.

The hydride and palladium compound catalyst of the present invention are easily available in the laboratory. This method is more convenient, much higher in safety. In addition, it is mild in condition but high in reaction yield.

EMBODIMENTS OF THE INVENTION

Example 1

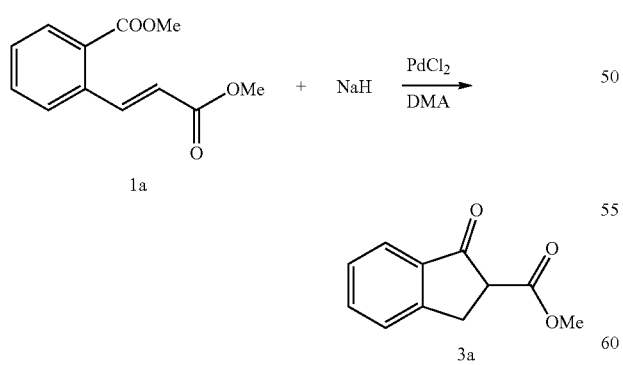

Under the protection of nitrogen, palladium chloride (5.3 mg, 0.03 mmol, 10 mol %) and sodium hydride (60% in oil, 24 mg, 0.6 mmol, 2 equiv) were stirred and suspended in DMA (1.5 mL) for 5 min at 25° C., and then the compound 1a (0.3 mmol) in DMA (0.5 mL) was added. The reaction was conducted at 25° C. for 2 h. The reaction was quenched by adding a saturated aqueous ammonium chloride solution. The product was subjected to extraction with ethyl acetate, combining the extract, drying with sodium sulphate, rotary evaporation, and column chromatography to obtain the product 3a with a yield is >99%. The mixture of enol and keto form, enol/keto=16/84. $^1$H NMR (400 MHz, CDCl$_3$): δ 10.37 (br, 1H, enol), 7.78 (d, J=7.6 Hz, 1H), 7.63 (t, J=7.2 Hz, 1H), 7.53-7.35 (m, 2H), 3.86 (s, 3H, enol), 3.79 (s, 3H, keto), 3.74 (dd, J=8.1, 3.9 Hz, 1H, keto), 3.57 (dd, J=17.3, 3.4 Hz, 1H, keto), 3.52 (s, 2H, enol), 3.38 (dd, J=17.2, 8.2 Hz, 1H, keto). 13C NMR (151 MHz, CDCl3): δ 199.58, 169.68, 153.73, 143.33 (enol), 135.61, 135.32 (enol), 129.54 (enol), 127.97, 126.97 (enol), 126.68, 124.86, 120.89, 102.30 (enol), 53.27, 52.95, 51.39 (enol), 32.65 (enol), 30.40. LR-MS (ESI): m/z 191.2 [M+H]+.

Example 2

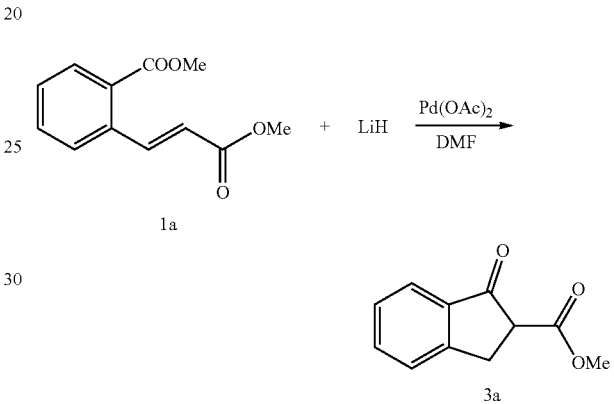

Under the protection of nitrogen, palladium acetate (2.7 mg, 0.015 mmol, 5 mol %) and lithium hydride (7.2 mg, 0.9 mmol, 3.0 equiv) were stirred and suspended in DMF (1.5 mL) for 5 min at 25° C., and then the compound 1a (0.3 mmol) in DMF (0.5 mL) was added. The reaction was conducted at 100° C. for 0.3 h. The reaction was quenched by adding a saturated aqueous ammonium chloride solution. The product was subjected to extraction with ethyl acetate, combining the extract, drying with sodium sulphate, rotary evaporation, and column chromatography to obtain the product 3a with a yield is 91%.

Example 3

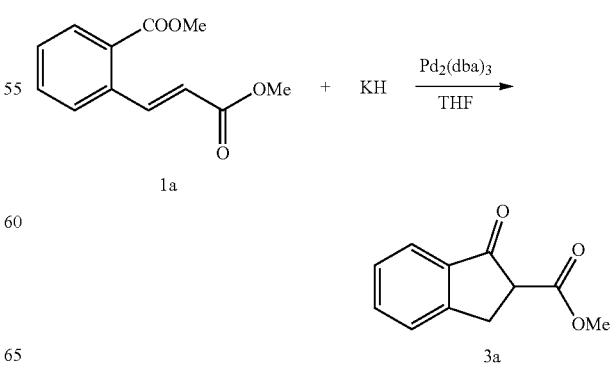

Under the protection of nitrogen, Pd$_2$(dba)$_3$ (2.7 mg, 0.003 mmol, 1 mol %) and potassium hydride (30% in oil, 200 mg, 1.5 mmol, 5 equiv) were stirred and suspended in THF (1.5 mL) for 5 min at 25° C., and then the compound 1a (0.3 mmol) in THF (0.5 mL) was added. The reaction was conducted at 0° C. for 10 h. The reaction was quenched by adding a saturated aqueous ammonium chloride solution. The product was subjected to extraction with ethyl acetate, combining the extract, drying with sodium sulphate, rotary evaporation, and column chromatography to obtain the product 3a with a yield is 82%.

Example 4

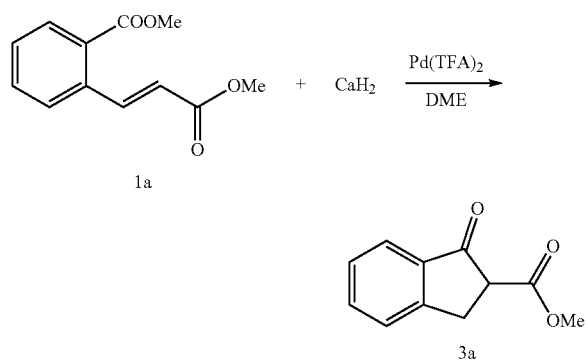

Under the protection of nitrogen, Pd(TFA)$_2$ (100 mg, 0.3 mmol, 100 mol %) and calcium hydride (24 mg, 0.6 mmol, 2.0 equiv) were stirred and suspended in DME (1.5 mL) for 5 min at 25° C., and then the compound 1a (0.3 mmol) in DME (0.5 mL) was added. The reaction was conducted at 90° C. for 0.3 h. The reaction was quenched by adding a saturated aqueous ammonium chloride solution. The product was subjected to extraction with ethyl acetate, combining the extract, drying with sodium sulphate, rotary evaporation, and column chromatography to obtain the product 3a with a yield of 83%.

Example 5

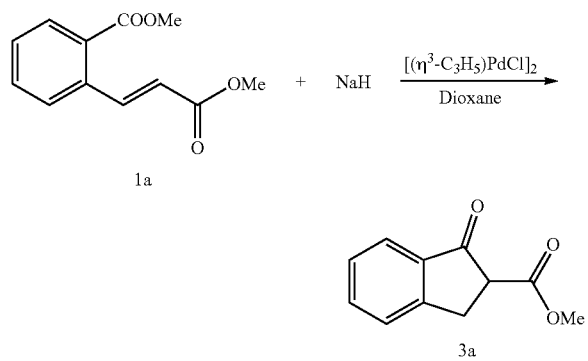

Under the protection of nitrogen, [(η$^3$-C$_3$H$_5$)PdCl]$_2$ (2.1 mg, 0.006 mmol, 2 mol %) and sodium hydride (60% in oil, 12 mg, 0.30 mmol, 1.0 equiv) were stirred and suspended in dioxane (1.5 mL) for 5 min at 25° C., and then the compound 1a (0.3 mmol) in dioxane (0.5 mL) was added. The reaction was conducted at 30° C. for 2 h. The reaction was quenched by adding a saturated aqueous ammonium chloride solution. The product was subjected to extraction with ethyl acetate, combining the extract, drying with sodium sulphate, rotary evaporation, and column chromatography to obtain the product 3a with a yield of 65%.

Example 6

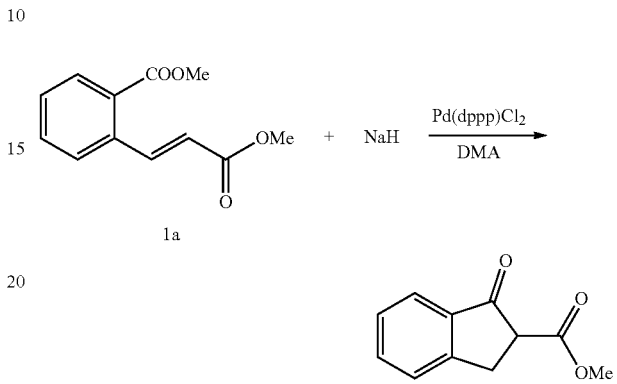

Under the protection of nitrogen, Pd(dppp)Cl$_2$ (18 mg, 0.03 mmol, 10 mol %) and sodium hydride (60% in oil, 24 mg, 0.6 mmol, 2 equiv) were stirred and suspended in DMA (1.5 mL) for 5 min at 25° C., and then the compound 1a (0.3 mmol) in DMA (0.5 mL) was added. The reaction was conducted at 25° C. for 2 h. The reaction was quenched by adding a saturated aqueous ammonium chloride solution. The product was subjected to extraction with ethyl acetate, combining the extract, drying with sodium sulphate, rotary evaporation, and column chromatography to obtain the product 3a with a yield of 63%.

Example 7

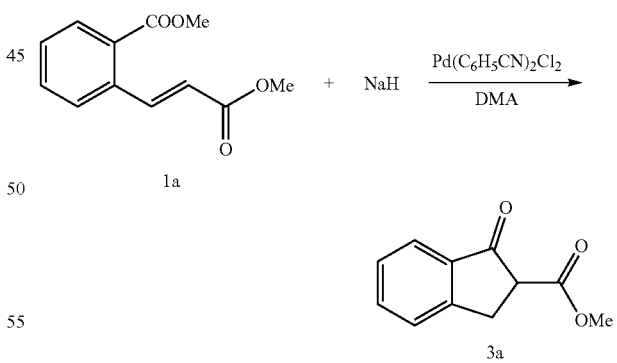

Under the protection of nitrogen, Pd(C$_6$H$_5$CN)$_2$Cl$_2$ (11.4 mg, 0.03 mmol, 10 mol %) and sodium hydride (60% in oil, 24 mg, 0.6 mmol, 2 equiv) were stirred and suspended in DMA (1.5 mL) for 5 min at 25° C., and then the compound 1a (0.3 mmol) in DMA (0.5 mL) was added. The reaction was conducted at 25° C. for 2 h. The reaction was quenched by adding a saturated aqueous ammonium chloride solution. The product was subjected to extraction with ethyl acetate, combining the extract, drying with sodium sulphate, rotary evaporation, and column chromatography to obtain the product 3a with a yield of 77%.

Example 8

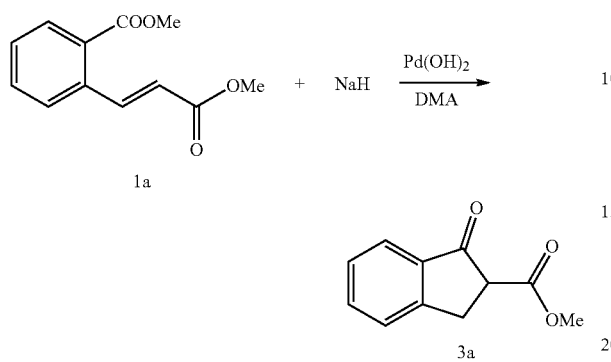

Under the protection of nitrogen, Pd(OH)$_2$ (4.2 mg, 0.03 mmol, 10 mol %) and sodium hydride (60% in oil, 24 mg, 0.6 mmol, 2 equiv) were stirred and suspended in DMA (1.5 mL) for 5 min at 25° C., and then the compound 1a (0.3 mmol) in DMA (0.5 mL) was added. The reaction was conducted at 25° C. for 2 h. The reaction was quenched by adding a saturated aqueous ammonium chloride solution. The product was subjected to extraction with ethyl acetate, combining the extract, drying with sodium sulphate, rotary evaporation, and column chromatography to obtain the product 3a with a yield of 69%.

Example 9

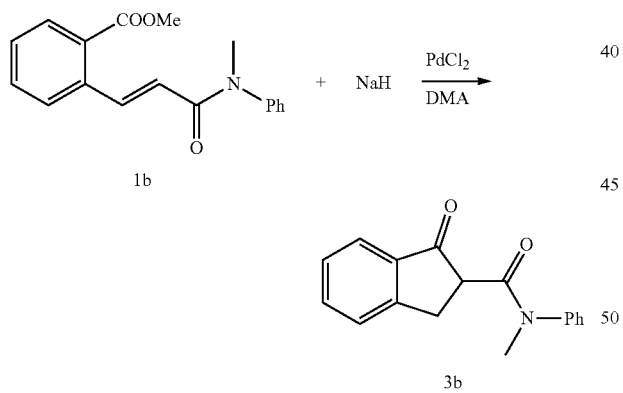

Under the protection of nitrogen, palladium chloride (5.3 mg, 0.03 mmol, 10 mol %) and sodium hydride (60% in oil, 24 mg, 0.6 mmol, 2 equiv) were stirred and suspended in DMA (1.5 mL) for 5 min at 25° C., and then the compound 1b (0.3 mmol) in DMA (0.5 mL) was added. The reaction was conducted at 25° C. for 2 h. The reaction was quenched by adding a saturated aqueous ammonium chloride solution. The product was subjected to extraction with ethyl acetate, combining the extract, drying with sodium sulphate, rotary evaporation, and column chromatography to obtain the product 3b with a yield of 98%. $^1$H NMR (400 MHz, CDCl$_3$): δ 7.69 (d, J=7.6 Hz, 1H), 7.59-7.40 (m, 6H), 7.38-7.29 (m, 2H), 3.74 (dd, J=8.0, 4.3 Hz, 1H), 3.56 (dd, J=16.9, 3.9 Hz, 1H), 3.37 (s, 3H), 3.13 (dd, J=16.8, 8.1 Hz, 1H). $^{13}$C NMR (151 MHz, CDCl$_3$): δ 202.19, 169.67, 154.41, 143.94, 135.80, 135.10, 129.94, 128.24, 127.95, 127.61, 126.46, 124.42, 51.10, 37.92, 31.80. LR-MS (ESI): m/z 266.1 [M+H]+.

Example 10

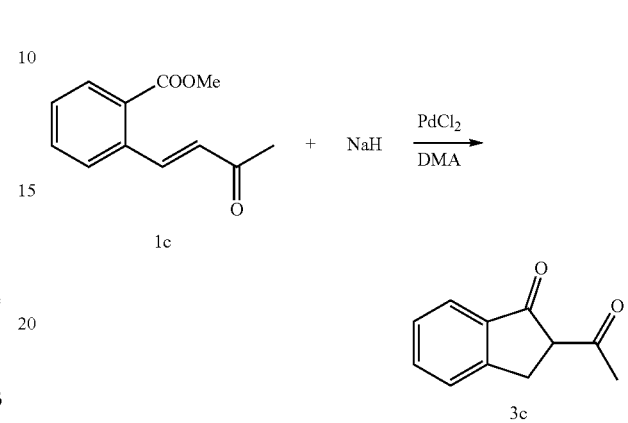

Under the protection of nitrogen, palladium chloride (5.3 mg, 0.03 mmol, 10 mol %) and sodium hydride (60% in oil, 24 mg, 0.6 mmol, 2 equiv) were stirred and suspended in DMA (1.5 mL) for 5 min at 25° C., and then the compound 1c (0.3 mmol) in DMA (0.5 mL) was added. The reaction was conducted at 25° C. for 2 h. The reaction was quenched by adding a saturated aqueous ammonium chloride solution. The product was subjected to extraction with ethyl acetate, combining the extract, drying with sodium sulphate, rotary evaporation, and column chromatography to obtain the product 3c with a yield of 98%. The mixture of enol and keto form, enol/keto=84/16. $^1$H NMR (400 MHz, CDCl$_3$): δ 7.81 (d, J=7.6 Hz, 1H, enol), 7.72 (d, J=7.6 Hz, 1H, keto), 7.63-7.46 (m, 2H, enol and keto), 7.44-7.33 (m, 1H, enol and keto), 4.11-3.92 (m, 1H, keto), 3.77-3.68 (m, 1H, keto), 3.58 (s, 2H, enol), 3.12 (dd, J=17.4, 7.7 Hz, 1H, keto), 2.49 (s, 3H, keto), 2.17 (s, 3H, enol). $^{13}$C NMR (151 MHz, CDCl3): δ 201.52 (keto), 199.85 (keto), 191.56, 177.60, 154.24 (keto), 147.63, 138.31, 135.52 (keto), 135.14 (keto), 132.88, 127.76 (keto), 127.43, 126.73 (keto), 125.85, 124.61 (keto), 123.28, 110.56, 62.07 (keto), 30.38, 29.82 (keto), 28.00 (keto), 21.18. LR-MS (ESI): m/z 175.1 [M+H]+.

Example 11

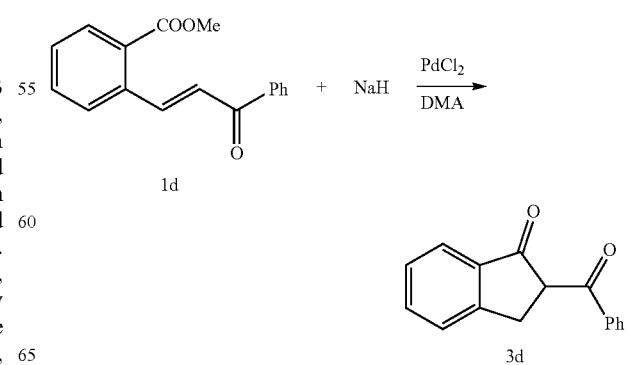

Under the protection of nitrogen, palladium chloride (5.3 mg, 0.03 mmol, 10 mol %) and sodium hydride (60% in oil, 24 mg, 0.6 mmol, 2 equiv) were stirred and suspended in DMA (1.5 mL) for 5 min at 25° C., and then the compound 1d (0.3 mmol) in DMA (0.5 mL) was added. The reaction was conducted at 25° C. for 2 h. The reaction was quenched by adding a saturated aqueous ammonium chloride solution. The product was subjected to extraction with ethyl acetate, combining the extract, drying with sodium sulphate, rotary evaporation, and column chromatography to obtain the product 3d with a yield of 99%. The mixture of enol and keto form, enol/keto=87/13. $^1$H NMR (400 MHz, CDCl$_3$): δ 15.08 (br, 1H, enol), 8.14 (d, J=7.6 Hz, 2H, keto), 8.00-7.92 (m, 2H, enol), 7.89 (d, J=7.6 Hz, 1H, enol), 7.73 (d, J=7.6 Hz, 1H, keto), 7.62-7.48 (m, 5H, enol and keto), 7.44 (t, J=7.2 Hz, 1H, enol), 7.40-7.35 (m, 1H, keto), 4.87 (dd, J=7.4, 2.6 Hz, 1H, keto), 3.94 (s, 2H, enol), 3.90-3.75 (m, 1H, keto), 3.34 (dd, J=17.1, 7.7 Hz, 1H, keto). $^{13}$C NMR (151 MHz, CDCl3): δ 200.12 (keto), 195.95, 194.40 (keto), 170.91, 154.47 (keto), 148.70, 145.81 (keto), 138.03, 136.43 (keto), 135.41 (keto), 134.94 (keto), 133.68 (keto), 133.47, 131.40, 129.96, 128.74, 128.25, 127.83 (keto), 127.59, 126.65 (keto), 125.73, 124.77(keto), 123.57, 109.58, 56.69 (keto), 32.37, 30.20 (keto). LR-MS (ESI): m/z 237.0 [M+H]+.

The invention claimed is:

1. A method of preparing a 1,3-dicarbonyl compound comprising:
   under the protection of nitrogen, suspending a palladium compound and a metal hydride in a solvent to form a mixture;
   adding an electron-deficient olefinic compound to the mixture;
   stirring the mixture at 0° C. to 100° C. for 0.3 to 10 hours to obtain the 1,3-dicarbonyl compound.

2. The method according to claim 1, wherein the metal hydride is sodium hydride, lithium hydride, potassium hydride, or calcium hydride; and the palladium compound is palladium chloride, palladium acetate, Pd$_2$(dba)$_3$, Pd(TFA)$_2$, [(η$^3$-C$_3$H$_5$)PdCl]$_2$, Pd(dppp)Cl$_2$, Pd(C$_6$H$_5$CN)$_2$Cl$_2$, or Pd(OH)$_2$.

3. The method according to claim 2, wherein the metal hydride is sodium hydride or lithium hydride; and the palladium compound is palladium chloride or palladium acetate.

4. The method according to claim 3, wherein the metal hydride is sodium hydride; and the palladium compound is palladium chloride.

5. The method according to claim 1, wherein the electron-deficient olefin compound has the following structure:

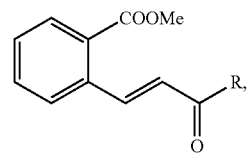

R is an aryl, an alkyl, an alkoxy, or an amino group.

6. The method according to claim 1, wherein a molar ratio of the palladium compound:the metal hydride:the electron-deficient olefin compound is (0.01 to 1):(1 to 5):1.

7. The method according to claim 6, wherein the molar ratio of the palladium compound:the metal hydride:the electron-deficient olefin compound is (0.05 to 0.15):(1 to 3):1.

8. The method according to claim 1, further comprising:
   adding a saturated ammonium chloride aqueous solution to the mixture to quench reaction; and
   conducting extraction, drying, rotary evaporation, and column chromatography to obtain the 1,3-dicarbonyl compound.

9. The method according to claim 1, wherein the solvent is DMA (dimethylacetamide), DMF (dimethylformamide), THF (tetrahydrofuran), DME (dimethoxyethane), or dioxane.

10. The method according to claim 1, wherein the mixture is stirred at 25 to 60° C. for 0.3 to 2 h.

* * * * *